(12) United States Patent
Edwards et al.

(10) Patent No.: US 6,627,785 B1
(45) Date of Patent: Sep. 30, 2003

(54) WOUND DRESSINGS WITH PROTEASE-LOWERING ACTIVITY

(75) Inventors: J. Vincent Edwards, Mandeville, LA (US); Robert F. Diegelmann, Richmond, VA (US); I. Kelman Cohen, Varina, VA (US); Dorne R. Yager, Chesterfield, VA (US)

(73) Assignees: Virginia Commwealth University, Richmond, VA (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/515,172

(22) Filed: Feb. 29, 2000

(51) Int. Cl.$^7$ ................................................. A61F 13/00
(52) U.S. Cl. ........................................................ 602/48
(58) Field of Search .............................. 602/41, 42, 48; 424/443–449

(56) References Cited

U.S. PATENT DOCUMENTS

| | | | | |
|---|---|---|---|---|
| 4,791,063 A | * | 12/1988 | Hou et al. | 435/243 |
| 5,187,153 A | | 2/1993 | Cordell et al. | 514/12 |
| 5,196,196 A | * | 3/1993 | Scott et al. | 424/94.64 |
| 5,488,160 A | * | 1/1996 | Morrissey | 564/165 |
| 5,733,563 A | * | 3/1998 | Fortier | 424/422 |
| 5,773,430 A | | 6/1998 | Simon et al. | 514/152 |
| 5,972,366 A | * | 10/1999 | Haynes et al. | 424/442 |
| 6,103,498 A | * | 8/2000 | Lawrence et al. | 435/69.2 |
| 6,156,334 A | | 12/2000 | Meyer-Ingold | 424/443 |
| 6,326,359 B1 | * | 12/2001 | Monaghan et al. | 514/46 |
| 2002/0044941 A1 | * | 4/2002 | Rosen et al. | |

* cited by examiner

Primary Examiner—Kim M. Lewis
(74) Attorney, Agent, or Firm—Whitham, Curtis & Christofferson, P.C.

(57) ABSTRACT

Sequestrants and inhibitors of protease are applied to the wound site through the use of wound dressing based carrier systems to which they may be optionally ionically or covalently bound for the purpose of the initiation or enhancement of healing associated with chronic non-healing wounds.

6 Claims, No Drawings

WOUND DRESSINGS WITH PROTEASE-LOWERING ACTIVITY

BACKGROUND OF THE INVENTION

1. Field of the Invention

The invention relates to the application of sequestrants and inhibitors of protease to wounds for the purpose of enhanced healing. The invention also relates to the inclusion of these active agents in wound dressings to which they may be, either compositioned or bound by covalent or ionic means for the purpose of controlled release or sequestration.

2. Description of the Prior Art

A wound of the skin is any degradation of its normal structure and function resulting from an internal or external pathology. A healing wound has aspects relating to control of infection, resolution of inflammation, angiogenesis, regeneration of a functional connective tissue matrix, contraction, resurfacing, differentiation, and remodeling. Chronic wounds are wounds that don't heal in a timely process.

Chronic wounds represent a worldwide health problem. Chronic wounds are a growing health care problem largely due to increasing longevity of the American population. Pressure or decubitus ulcers which are a type of chronic wound represent an estimated 3% to 5% incidence in hospital patients. In patients with spinal chord injuries the incidence of chronic wounds is 25% to 85%. Approximately one million Americans hospitalized yearly will develop pressure sores resulting in a cost of 750 million dollars for patient care.

Elastase is perhaps the most destructive enzyme in the body and has been well characterized in non-healing wounds. An excessive concentration of both the serine protease elastase and matrix metalloproteinases (MMPs) in chronic non-healing wounds has been shown to deleteriously degrade cytokine growth factors, fibronectin, and endogenous levels of protease inhibitors necessary for healing. Although numerous studies with both animals and human beings have shown that growth factors may accelerate healing of chronic wounds, therapeutic attempts to modulate the wound healing response with them have had limited success.

The composition of the wound dressing is relevant to designing a mechanism-based approach to protease inhibition in the environment of the wound fluid. (Wiseman D M, Rovee, D T, Alvarez O M Wound dressing: design and use in Wound Healing Biochemical & Clinical Aspects, eds. Cohen I K, Diegelmann, R F, Lindbald, W J, 1992, Hartcourt Brace Jovanovich, Inc. 562–580). The fiber or gel composition of synthetic dressings, applied to chronic wounds, include synthetic hydrogel polymers, collagen, hydrocolloids, alginates and cotton and carboxymethylcellulose. Controlled release of agents linked with important roles in wound healing includes growth factors, antibiotics, and trace elements. The use of the enzyme inhibitor aprotinin for treatment of corneal ulcers was reported, however, there have been no known reports of treatment methods on the release of elastase inhibitors into wounds.

U.S. Pat. No. 5,098,417 to Yamazaki et al. teaches the ionic bonding of physiologically active agents to cellulosic wound dressings.

U.S. Pat. No. 4,453,939 to Zimmerman et al. teaches the inclusion of aprotonin in compositions for "sealing and healing" of wounds.

U.S. Pat. No. 5,807,555 to Bonte et al. teaches the inclusion of inhibitors for alpha-1-protease, collagenase, and elastase in pharmaceutical compositions for promotion of collagen synthesis.

U.S. Pat. No. 5,696,101 to Wu et al. teaches use of oxidized cellulose (e.g. oxycel) as a bactericide and hemostat in treatment of wounds.

World Patent WO 98/00180 to Watt et al. teaches complexation of oxidized cellulose with structural proteins (e.g. collagen) for chronic wound healing; and references the utility of oligosaccharide fragments produced by the breakdown of oxidized cellulose in vivo in the promotion of wound healing.

SUMMARY OF THE INVENTION

We have now discovered that direct application of protease inhibitors to wound sites promotes wound healing by amelioration of the deleterious effects of elastase on cytokines, endogenous anti-proteases, and fibronectin in the wound microenvironment. While not wanting to be bound thereto, it is Applicants' theory that the release of protease inhibitors into the chronic wound or modification of wound dressing fibers for selective protease sequestration may be beneficial in restoring the proteinase/antiproteinase balance needed to avoid degradation of growth factors and effectively accelerate healing of chronic wounds. The active agents are applied to the wound site in conjunction with known wound dressings, preferably polysaccharide based wound dressings. The invention includes methods of linking these protease inhibitors either covalently or ionically to wound dressings including polysaccharide containing matrices. Also described are formulations of the inhibitors onto fibers, the method of production of same, and pharmaceutical compositions which are effective in the treatment of mammalian chronic wounds.

Therefore, it is an object of this invention to provide methods and compositions for the enhanced treatment of mammalian wounds comprising the application of protease inhibitors.

Another object is to provide novel conjugates of protease inhibitors with wound dressings for use as sequestrants in wound environments.

A further object is to provide ionic systems for sustained release of protease inhibitors into the wound environment.

Other objects and advantages will become apparent from the ensuing description.

DETAILED DESCRIPTION OF THE INVENTION

The present invention is based upon the previously unrecognized discovery that inhibitors and sequestrants of proteases may be used as healing accelerants of chronic wounds. These may be physically applied on wound dressings, or in the alternative may be ionically or covalently conjugated to a wound dressing material for purposes of sustained release of active agent or sequestration of endogenous constituents from the wound environment. The term protease inhibitor is meant to include those materials which effect a diminution in protease activity in the wound environment.

Specific pharmacological effects of elastase inhibitors and sequences associated with wound dressings include inhibition of the breakdown of growth factors that stimulate migration of cells to the ulcer site of the wound leading to the growth of new tissue that heals the open wound. This technology is broadly applicable to all forms of chronic wounds including diabetic ulcers and decubitus bedsores. Both peripheral and central administration of the compounds formulated on wound dressings accelerate wound healing of chronic wounds. The compounds of this invention may be applied to wound dressings as agents that may be released into the wound and thereby inhibit human elastase and thus prevent growth factor and tissue degradation. Alternatively the inhibitors of this invention are covalently bound to the wound dressing. As a component of such a matrix, they are able to sequester destructive elastase from the microenvironment of the wound, thus preventing the degradation of growth factors and fibronectin that would otherwise occur.

The therapeutic administration of the modified wound dressings containing inhibitors include a pharmacologically effective dose of the inhibitor or sequestrant when used in the treatment of a patient in need thereof. The dose of inhibitor or sequestrant required on the wound dressing to promote accelerated healing in the patient ranges from about 0.2 mg/gram fiber to about 200 mg/gram fiber per day, with this in turn being dependent upon specific factors including patient health, wound type, and specific-protease inhibitor/sequestrant utilized. The amount of active agent required can be readily determined by those skilled in the art.

The term patient used herein is taken to mean mammals such as sheep, horses, cattle, pigs, dogs, cats, rats, mice and primates, including humans.

The term wound dressing used herein is taken to include any pharmaceutically acceptable wound covering such as:
a) films, including those of a semipermeable or a semi-occlusive nature such as polyurethane copolymers, acrylamides, acrylates, paraffin, polysaccharides, cellophane and lanolin.
b) hydrocolloids including carboxymethylcellulose, protein constituents of gelatin, pectin, and complex polysaccharides including Acacia gum, guar gum and karaya.
These materials may be utilized in the form of a flexible foam or, in the alternative, formulated in polyurethane or, in a further alternative, formulated as an adhesive mass such as polyisobutylene.
c) hydrogels such as agar, starch or propylene glycol; which typically contain about 80% to about 90% water and are conventionally formulated as sheets, powders, pastes and gels in conjunction with cross-linked polymers such as polyethylene oxide, polyvinyl pyrollidone, acrylamide, propylene glycol.
d) foams such as polysaccharide analogs which consist of a hydrophilic open-celled contact surface and hydrophobic closed-cell polyurethane
e) impregnates including pine mesh gauze, paraffin and lanolin-coated gauze, polyethylene glycol-coated gauze, knitted viscose, rayon, and polyester.
f) cellulose-like polysaccharides such as alginates, including calcium alginate, which may be formulated as non-woven composites of fibers or spun into woven composites.

Preferred wound dressings are polysaccharide-containing matrices capable of ionically or covalently bonding the active agents thereto, or having the active agent compositioned with or upon, and is envisioned to include chitosans, alginates and cotton or carboxymethylated cotton in the form of gauze, films, hydrocolloids, hydrogels, hydroactives, foams, impregnates, absorptive powders and pastes, as known in the art and described in USP 24:NF 19; The United States Pharmacopeia: The National Formulary, USP 24:NF 19, United States Pharmacopeial Convention, INC., Rockville, Md., Jan. 1, 2000, incorporated by reference herein.

Especially preferred wound dressings include cotton cellulose formed as woven or non-woven gauze wherein the protease sequestrant or inhibitor is linked to the cellulose polysaccharide chain through a chemical sustituent selected from the group consisting of amino, carboxylate, citrate, phosphate, sulfonate, chloride, bromide, mono-carboxylic acid, di-carboxylic acid, tri- carboxylic acid; or any pharmaceutically acceptable salt thereof. Exemplary salts are seen to include those of acids such as acetic, glycolic, lactic, pyruvic, malonic, succinic, glutaric, fumaric, malic, tartaric, ascorbic, maleic, hydroxymaleic, benzoic, hydroxybenzoic, phenylacetic, cinnamic, salicylic, and 2-phenoxybenzoic; and sulfonic acids such as methane sulfonic acid and hydroxyethane sulfonic acid. Salts of the carboxy terminal amino acid moiety may include the nontoxic carboxylic acid salts formed with any suitable inorganic or organic bases. Illustratively, these salts include those of alkali metals, as for example, sodium and potassium; alkaline earth metals, such as calcium and magnesium; light metals of Group IIA elements including aluminum; and organic primary, secondary, and tertiary amines, as for example, trialkylamines, including triethylamine, procaine, dibenzylamine, 1-ethenamine, N,N'-dibenzylethylenediamine, dihydroabietylamine, N-alkylpiperidine and any other suitable amine.

The active agents may be applied as a reactively bound constituent of a wound dressing or may be compositioned for application to a treatment site via moistened fibers in the dressing. Dressing systems may be either single or multi-phase; with the one-phase system consisting of the wound dressing with the active agent. An exemplary multi-phase system would employ the wound dressing and a suspension of a physiologically acceptable diluent. Exemplary pharmaceutical carriers which may function as the diluent can be a sterile physiologically acceptable liquids such as water and oils and may optionally further contain surfactants and other pharmaceutically acceptable adjuvants. An exemplary but non-exhaustive list of oils which can be employed in these preparations are those of petroleum, animal, vegetable, or synthetic origin, for example, peanut oil, soybean oil, and mineral oil. In general water, saline, and glycols, such as polyethylene glycols are preferred liquid carriers.

The present invention is thus viewed to encompass derivatives of wound dressings presented as formulas I and II below:

$$X—A \qquad (I)$$

wherein:
X is selected from:
a) films, including those of a semipermeable or a semi-occlusive nature such as polyurethane copolymers, acrylamides, acrylates, paraffin, polysaccharides, cellophane and lanolin;
b) hydrocolloids including carboxymethylcellulose, protein constituents of gelatin, pectin, and complex polysaccharides including Acacia gum, guar gum and karaya.
These materials may be utilized in the form of a flexible foam or, in the alternative, formulated in polyurethane or, in a further alternative, formulated as an adhesive mass such as polyisobutylene;
c) hydrogels such as agar, starch or propylene glycol; which typically contain about 80% to about 90% water and are conventionally formulated as sheets, powders, pastes and gels in conjunction with cross-linked polymers such as polyethylene oxide, polyvinyl pyrollidone, acrylamide, propylene glycol;

d) foams such as polysaccharide analogs which consist of a hydrophilic open-celled contact surface and hydrophobic closed-cell polyurethane;

e) impregnates including pine mesh gauze, paraffin and lanolin-coated gauze, polyethylene glycol-coated gauze, knitted viscose, rayon, and polyester;

f) cellulose-like polysaccharides such as alginates, including calcium alginate, which may be formulated as non-woven composites of fibers or spun into woven composites;

g) polysaccharide-containing matrices capable of ionically or covalently bonding the active agents thereto, or having the active agent compositioned with or upon, and is envisioned to include chitosans, alginates and-cotton or carboxymethylated cotton in the form of gauze, films, hydrocolloids, hydrogels, hydroactives, foams, impregnates, absorptive powders and pastes; and h) cotton cellulose formed as woven or non-woven gauze wherein the protease sequestrant or inhibitor is linked to the cellulose polysaccharide chain through a chemical sustituent selected from the group consisting of amino, carboxylate, citrate, phosphate, sulfonate, chloride, bromide, mono-carboxylic acid, di-carboxylic acid, tri-carboxylic acid; or any pharmaceutically acceptable salt thereof.

Exemplary salts are seen to include those of acids such as acetic, glycolic, lactic, pyruvic, malonic, succinic, glutaric, fumaric, malic, tartaric, ascorbic, maleic, hydroxymaleic, benzoic, hydroxybenzoic, phenylacetic, cinnamic, salicylic, and 2-phenoxybenzoic; and sulfonic acids such as methane sulfonic acid and hydroxyethane sulfonic acid. Salts of the carboxy terminal amino acid moiety may include the nontoxic carboxylic acid salts formed with any suitable inorganic or organic bases. Illustratively, these salts include those of alkali metals, as for example, sodium and potassium; alkaline earth metals, such as calcium and magnesium; light metals of Group IIA elements including aluminum; and organic primary, secondary, and tertiary amines, as for example, trialkylamines, including triethylamine, procaine, dibenzylamine, 1-ethenamine, N,N'-dibenzylethylenediamine, dihydroabietylamine, -alkylpiperidine and any other suitable amine.

A is selected from the group consisting of hydrogen, methyl, methyl chloroformate, pentafluoroethylketone, dihydroxylketone, levulinate, alkyl ketone, 2,3 dialdehyde anhydroglucose, glucose, glucose-6-citrate, 2,3 dialdehydo-glucose-6-citrate, an alkyl amino acid such as Ala, Leu, Ile, Val, and Nle, or a di- or tri-peptide sequence consisting of the following sequence: Val-Pro, Pro-Val, Ala-Pro-Val or Val-Pro-Ala or a tetrapeptide sequence wherein any of the following amino acids are the amino terminal residue of Ala-Pro-Val or Val-Pro-Ala; Lys, Arg, Trp, Phe, Gin, His, Tyr, and are linked through the amino- or COOH-termini of the peptide to X; with the proviso that when $A_1$ is an amino acid or peptide it may also be derivatized at its unbound amino- or COOH-terminus as an acid, carboxamide, alcohol, ester, ketone, aldehyde, ketomethylester, methyl chloroformate, pentafluoroethylketone or p-nitroanilide.

Compounds of formula II are of the structure:

$$X—B \qquad (II)$$

wherein:

X is selected from:

a) films, including those of a semipermeable or a semi-occlusive nature such as polyurethane copolymers, acrylamides, acrylates, paraffin, polysaccharides, cellophane and lanolin;

b) hydrocolloids including carboxymethylcellulose, protein constituents of gelatin, pectin, and complex polysaccharides including Acacia gum, guar gum and karaya.

These materials may be utilized in the form of a flexible foam or, in the alternative, formulated in polyurethane or, in a further alternative, formulated as an adhesive mass such as polyisobutylene;

c) hydrogels such as agar, starch or propylene glycol; which typically contain about 80% to about 90% water and are conventionally formulated as sheets, powders, pastes and gels in conjunction with cross-linked polymers such as polyethylene oxide, polyvinyl pyrollidone, acrylamide, propylene glycol;

d) foams such as polysaccharide analogs which consist of a hydrophilic open-celled contact surface and hydrophobic closed-cell polyurethane;

e) impregnates including pine mesh gauze, paraffin and lanolin-coated gauze, polyethylene glycol-coated gauze, knitted viscose, rayon, and polyester;

f) cellulose-like polysaccharides such as alginates, including calcium alginate, which may be formulated as non-woven composites of fibers or spun into woven composites;

g) polysaccharide-containing matrices capable of ionically or covalently bonding the active agents thereto, or having the active agent compositioned with or upon, and is envisioned to include chitosans, alginates and cotton or carboxymethylated cotton in the form of gauze, films, hydrocolloids, hydrogels, hydroactives, foams, impregnates, absorptive powders and pastes; and h) cotton cellulose formed as woven or non-woven gauze wherein the protease sequestrant or inhibitor is linked to the cellulose polysaccharide chain through a chemical sustituent selected from the group consisting of amino, carboxylate, citrate, phosphate, sulfonate, chloride, bromide, mono-carboxylic acid, di-carboxylic acid, tri-carboxylic acid; or any pharmaceutically acceptable salt thereof.

Exemplary salts are seen to include those of acids such as acetic, glycolic, lactic, pyruvic, malonic, succinic, glutaric, fumaric, malic, tartaric, ascorbic, maleic, hydroxymaleic, benzoic, hydroxybenzoic, phenylacetic, cinnamic, salicylic, and 2-phenoxybenzoic; and sulfonic acids such as methane sulfonic acid and hydroxyethane sulfonic acid. Salts of the carboxy terminal amino acid moiety may include the nontoxic carboxylic acid salts formed with any suitable inorganic or organic bases. Illustratively, these salts include those of alkali metals, as for example, sodium and potassium; alkaline earth metals, such as calcium and magnesium; light metals of Group IIA elements including aluminum; and organic primary, secondary, and tertiary amines, as for example, trialkylamines, including triethylamine, procaine, dibenzylamine, 1-ethenamine, N,N'-dibenzylethylenediamine, dihydroabietylamine, N-alkylpiperidine and any other suitable amine.

B is selected from the group consisting of an alkyl amino acid such as Ala, Leu, Ile, Val, and Nle; a di- or tri-peptide sequence consisting of Val-Pro, Pro-Val, Ala-Pro-Val or Val-Pro-Ala; or a tetrapeptide sequence containing Ala-Pro-Val or Val-Pro-possessing as a terminal residue amino acids selected from Ala, Lys, Arg, Trp, Phe, Gln, His, and Tyr; and wherein the substituent is linked, through the amino- or COOH-termini of the peptide, to X via a salt bridge, or are embedded in the cotton cellulose fiber; with the proviso that when $A_1$ is an amino acid or peptide, it may also be derivatized at its unbound amino- or COOH-terminus as an acid, carboxamide, alcohol, ester, ketone, aldehyde, ketomethylester, methyl chloroformate, pentafluoroethylketone, or p-nitroanilide. $B_1$ may also be alpha-antitrypsin or any protein serine protease inhibitor bound through a salt bridge to the derivatized cotton cellulose. In a similar manner $B_1$ may be an antibiotic such as doxycycline or cephalosporin linked via a salt bridge or embedded in the cotton fiber.

This invention is illustrated by the following nonlimiting examples.

EXAMPLE 1

General Synthesis and Formulation of Conlugates of Cotton Cellulose and Inhibitor Sequences Desized, scoured, and bleached cotton gauze was used for the synthesis. The fabric was also mercerized prior to the synthesis. The cotton twill fabric was cut as circular discs (8.5 cm. in diameter) for the synthesis. Carboxymethylated cotton cellulose was prepared by refluxing 100% cotton twill (290 grams) for one hour with 25% monochloroacetic acid in a sodium hydroxide solution of methanol:isopropanol (13:87, v:v) and 0.5% TX-100. The degree of substitution of carboxymethylation or carboxyl content was determined by measuring the carboxyl content of the cotton with an acid base titration. The carboxyl content was calculated from the following equation:

$$DS = \frac{(162)\,(\%\text{ COOH})}{4500 - (R)\,(\%\text{ COOH})}$$

where R is the molecular weight of the ether sustituent minus one i.e., 58 for carboxymethylcellulose.

Fmoc-amino acids were purchased from Peptides International (Louisville Ky.).

Esterification of the cotton cellulose was accomplished through base-catalyzed carbodiimide/HOBT acylation. Cotton samples used in the synthesis were pre-treated with 20 mL 25% TFA/DCM (10 min), washed with 5×20 mL DCM, 2×20 mL, 10% DIPEA, 5×20 mL (5 min), and 2×20 mL DCM. The cotton discs were vacuum dried on a Buchner funnel, and esterified in a beaker placed in an ultrasonic bath. Fmoc-glycine esterification was accomplished by reacting the cotton discs in a 20 mL DMF solution with 0.3M Fmoc-Glycine/DIC/HOBT and 0.03 DMAP. The cotton discs were washed with DMF and water and glycine estimated from amino acid analysis to be 200 micromoles/gram of cotton. Cotton samples of this type prepared with glycine linkers may then be used to assemble peptide sequences as shown in example 2 or may be used to form the counterion of a peptide or amino acid carboxy salt. Thus the amino salts of glycine cotton cellulose conjugates may be formed with elastase peptide inhibitors illustrative of the claims.

EXAMPLE 2

Peptide Synthesis on Cotton Cellulose

The Val-Pro-Val recognition sequence was synthesized with glycine as a COOH-terminal linker on 8.5 cm discs of cotton twill. The synthetic protocol for the synthesis of Val-Pro-Val-Gly on cotton consisted of the following steps as described by Eichler. Acetylation of Fmoc-Gly-bound cellulose cotton was accomplished with acetic anhydride/NMI/DMF 1:2:3 (v/v/v) for 60 min. The cotton discs were washed with DMF (3×10 mL) and DCM (2×10 mL). Deprotection of Fmoc was accomplished in 20% piperidine/DMF, 15 min; wash (3×DMF, 2×DCM); coupling (0.3M Fmoc-amino acid/HOBT/DIC in DMF, 90 min); wash (3×DMF; 2×DCM). Ten microliters of a bromophenol blue/DMF solution was added during the coupling step. Two hundred milligram samples were subjected to amino acid analysis. The resulting ratios of amino acids from the analysis was 1:2 (Pro:Val) and the resulting yield was 1.1 micromoles/gram cotton. The resulting peptido-cellulose conjugate of cotton gauze as shown in example 11 retains the enzyme elastase when the cotton conjugates are subject to elastase solutions, and therefore the Val-Pro-Val-cellulose conjugates serve as sequestrants useful in clearing wound fluid of high elastase activity.

EXAMPLE 3

Synthesis of Val-Pro-Val-O-Methylester

A solution of Carbobenzoxy-Val-Pro-OH (1 g, 2.8 mmol) in 30 mL of dry tetrahydrofuran was cooled to −5° C. and N-methylmorpholine (0.29 g, 2.8 mmol) and isobutyl chloroformate (0.391 9, 2.8 mmol) were added and stirred for 1 h. A solution of Val-OMe (0.49 9, 2.8 mmol) in dioxane/water (7:3) was adjusted to pH 7 with diisopropylethylamine. The solutions were combined and the mixture stirred for 3 h, water added and the tetrahydrofuran evaporated. The resulting oil was extracted with ethyl acetate and subjected to a work-up of 1 N HCl, saturated NaCl, and drying over sodium sulfate yielding a clear oil. The product was confirmed by FAB MS ([M+1]=461) and the N-protecting group was removed by catalytic hydrogenolysis using ammonium formate. (Anwer, M. K., & Spatola, A. F. (1980) Synthesis 11, 929–932). The product Val-Pro-Val-OMe may be used in the formation of carboxymethylcellulose-Val-Pro-Val-OMe conjugate as outlined in example 4, or it may be embedded in the fibers of wound dressings as outlined in example 11.

EXAMPLE 4

Synthesis of Carboxymethylcellulose-Val-Pro-Val-OMe Conjugate

Two carboxymethylated cotton discs (circular 8.5 cm discs weighing 2.6 g each with a degree of substitution, 25%) were reacted with 0.15M Val-Pro-Val-OMe/HOBT/DIC in 10 mL DMF mixed in a beaker and placed in an ultrasonic bath. The reaction was monitored with bromophenol blue (20 uL, 0.01 M bromophenol), and was allowed to proceed overnight. Conversion of blue to yellow signals completion of the reaction. Three hundred milligram samples of the cotton cellulose conjugates were subject to amino acid analysis. The resulting ratio of amino acid from the analysis was 1:2 (Pro:Val) and the resulting yield was 0.484 micromoles/gram cotton. The peptido-cellulose conjugate of cotton as shown in example 11 retains elastase in solution and clears wound fluid of elastase activity.

EXAMPLE 5

Preparation of 2,3 Dialdehyde-anhydroglucos-cellulose, Sulfonated, and Phosphorylated Cotton Cotton gauze (12 ply-4in.×4in.), USP type VII, was treated in lots of 50 gauze sponges in a 0.07 M solution of sodium periodate for 1 h at 45° C. with a solution pH of 4.2. Following the treatment excess periodate was removed by rinsing the gauze through a screen under running tap water. Following the rinse cycle the gauze were passed through a conventional ringer to remove excess moisture. The samples were then separated and placed on a wire rack to air dry overnight. The dried gauze are placed in a chex all II instant sealing pouch (5 in.×10 in.) and sterilized with ethylene oxice gas by Micro Test Laboratories, Agauam, Mass.

The cotton gauze may be sulfonated by washing the dialdehyde oxycellulose with 5% sodium bisulfite (NaHSO3) under pH4.5, liquor ratio 1:60 for 3 hours. Excess sodium bisulfite may be removed by rinsing with water under running tap water. Following the rinse cycle the gauze are passed through a conventional ringer to remove excess moisture. The samples are then separated and place on a wire rack to air dry overnight.

Phosphorylation of cotton gauze is accomplished by applying inorganic phosphate salt to cotton gauze in 4–16% composition. Urea is usually included in the formulation on a 2:1 weight ratio of urea to phosphate. All formulations contained 0.1% Triton X-100 as a wetting agent. The cotton gauze is padded to 80–90% wet pickup and then dried at 60° C. The samples are cured at 160° C. for 7 min.

The phosphorylated and sulfonated cotton cellulose D.S. levels were 0.035 and 0.011 respectively as measured by elemental analysis.

Gauze containing the above finishes and prepared in this manner have been demonstrated to lower elastase activity in wound fluid as shown in example 11.

EXAMPLE 6

Preparation of Carboxymethylcellulose-Ala-Ala-Pro-Valine-chloromethylketone

A stirred suspension of N-tosyl-L-valine acid chloride (0.95 g, 3 mmoles) in anhydrous ether (30 mL) was treated in an ice bath with ethereal diazomethane (6 mmoles) in anhydrous ether. The reaction mixture was left overnight, then treated with dry hydrogen chloride for 2 h. The chloroketone is obtained on removal of the solvent.

A solution of Carbobenzoxy-Ala-Ala-Pro-OH (2.8 mmol) in 30 mL of dry tetrahydrofuran was cooled to −5° C. and N-methylmorpholine (0.29 g, 2.8 mmol) and isobutyl chloroformate (0.391 g, 2.8 mmol) were added and stirred for 1 h. A solution of N-tosyl-L-valine chloromethylketone (2.8 mmol) in dioxane/water (7:3) was adjusted to pH 7 with diisopropylethylamine. The solutions were combined and the mixture stirred for 3 h, water added and the tetrahydrofuran evaporated. The resulting oil was extracted with ethyl acetate and subjected to a work-up of 1N HCl, saturated NaCl, and drying over sodium sulfate yielding a clear oil. The N-protecting group was removed by catalytic hydrogenolysis using ammonium formate. The resulting product was filtered and lyophilized to give the peptide Ala-Ala-Pro-Val-chloromethylketone. Two carboxymethylated cotton discs (circular 8.5 cm discs weighing 2.6 g each with a degree of substitution, 25%) were reacted with Ala-Ala-Pro-Val-pentafluoroethylketone/HOBT/DIC in 10 mL DMF mixed in a beaker and placed in an ultrasonic bath. The reaction was monitored with bromophenol blue (20 uL, 0.01 M bromophenol), and was allowed to proceed overnight. Conversion of blue to yellow signals completion of the reaction. Three hundred milligram samples of the cotton cellulose conjugates were subject to amino acid analysis. The resulting ratio of amino acid from the analysis was 2:1:1 (Ala:Pro:Val) and the resulting yield was 0.484 micromoles/gram cotton. The resulting chloromethyleketone conjugate of cellulose cotton may be used to clear elastase from wound fluid as shown in example 11.

EXAMPLE 7

Preparation of Carboxymethylcellulose-Ala-Ala-Pro-Val-Dentafluoroethylketone Boc-Valyl-N-methyl-O-Methylcarboxamide.

To a solution of N-(tert-butoxycarbonyl)-L-valine in methylene chloride was added dimethylaminopyridine, N,O,-dimethylhydroxylamine hydrochloride, NMM and EDCI and the solution was stirred at room temperature for 20 h. The solution was washed with 10% HCl, saturated NaHCO3 and brine, and the solvent was removed in vacuo to give a colorless oil.

Boc-Valyl-pentafluoroethylketone.

To a −78° C. solution of Boc-Valyl-N-methyl-methylcarboxamide was added condensed pentafluoroethyliodide. To the mixture was added methyllithium-lithium bromide complex while maintaining an internal reaction temperature below −65° C. The reaction mixture is stirred at −65° to −78° for 1.5 h. The mixture was poured into water and the aqueous phase was acidified with potassium hydrogen sulfate. The aqueous phase was extracted with additional Et2O (500 mL), and the combined organic extracts were washed with saturated NaHCO3 and dried over Na2SO4.

Boc-Ala-Ala-Pro-Val-Pentafluoroethylketone.

A solution of Boc-Valyl-pentafluoroethylketone in trifluoroacetic acid: methylene chloride (1:1, v:v) was prepared and allowed to react for 30 min. The solvent was removed in vacuo and the resulting deprotected peptide reacted with Boc-Ala-Ala-Pro-OH through diisopropycarbodiimide/HOBT coupling.

Further preparation of carboxymethyl cellulose-O-Ala-Ala-Pro-Val-pentafluoroethylketone is as follows:

Two carboxymethylated cotton discs (circular 8.5 cm discs weighing 2.6 g each with a degree of substitution, 25%) were reacted with 0.15M Ala-Ala-Pro-Val-chloromethylketone/HOBT/DIC in 10 mL DMF mixed in a beaker and placed in an ultrasonic bath. The reaction was monitored with bromophenol blue (20 uL, 0.01 M bromophenol), and was allowed to proceed overnight. Conversion of blue to yellow signals completion of the reaction. The cotton is then washed with 20 mL of DMF three times followed by three washes with methylene chloride×3. The resulting peptido-cellulose conjugates on cotton were subject to amino analysis and found to contain 30 micromoles of peptide per gram of cotton. The resulting cotton conjugates may be utilized as shown in sample 11 to clear wound fluid of elastase activity.

EXAMPLE 8

Preparation of Propyl-3-keto-(2,3,6)-O-Cellulose Ether

Four grams of cotton cellulose is suspended in a 300 mL solution of dioxane and water (2:1) whereupon Dabco (1,4-diazabicyclo[2.2.2]octane) is added to pH 8 and 0.0246 moles of vinylpropylketone is added and the suspension allowed to stir for overnight. Alternatively the treated gauze soaked with the solution of base and vinylpropyketone, may be cured at 100° C. for one hour and the product rinsed with cold water for 30 minutes followed by drying at 85° C. The cotton gauze finishes of this modification demonstrate elastase-lowering activity as shown in example 11.

EXAMPLE 9

Preparation of Levulinate-(2,3,6)-O-Cellulose Ester

Preparation of Levulinate-(2,3,6)-O-Cellulose ester Esterification of cotton cellulose gauze with levulinic acid was accomplished by reacting the cotton discs in a 20 mL DMF solution with 0.3M levulinic acid/DIC/HOBT and 0.03 DMAP. The esterification may also be performed under aqueous conditions with a water soluble carbodiimide at the same molar concentrations given or through convention pad and cure techniques employing citric acid and sodium hypophosphite crosslinking of the levulinic acid as outlined with example 10. The cotton gauze finishes of this modification demonstrate elastase-lowering activity as outlined in example 11.

EXAMPLE 10

Preparation of Glucose-6-citrate-(2,3,6)-O-Cellulose Ester

Two gram samples of cotton gauze were padded with two dips and two nips in a four percent solution of sodium hypophosphite, a 0.62M citric acid and a 0.12M glucose solution on a laboratory mangle. The padded gauze were dried and cured in ovens with mechanical circulated air. Curing temperatures were set at 180° C., and drying at 85° C. The resulting add-on weight of product was found to be 11% or an 11% increase in weight based on the difference before and after the wet finishing modification. The resulting cotton gauze was shown to possess elastase-lowering activity in wound fluid as demonstrated in example 11.

EXAMPLE 11

Ten milligrams of Ala-Pro-Val-Chloromethylketone acetate salt was dissolved in a 0.05 M saline solution and applied to 2 grams of carboxymethylated cotton gauze to saturation. The gauze was then lyophlized to dryness and a cotton cellulose sample taken for amino acid analysis revealing 10 micromoles of peptide per gram of cotton gauze.

Patients and Wound Fluids

Fluids were harvested from seven-grade III sacral, ischial, or trochanteric pressure ulcers of five patients with spinal cord injuries. Three patients had two distinct wounds which were sampled and which were considered separate data points. Patients ranged in age from 50–65 years and had no significant comorbidities. All wounds were present for a minimum of 2 months. There was no evidence of gross infection in any of the wounds used in the study. Wound care in all but one ulcer consisted of normal saline-soaked wet to dry dressings. A small margin of one wound was receiving topical collagenase (Santyl) for enzymatic debridement. This wound was irrigated copiously with normal saline prior to collection of ulcer fluid. An occlusive dressing (Tegaderm: 3M, St Paul, Minn.) was placed over the ulcers for 2–4 hours, and fluid was collected by aspiration with a sterile tuberculin syringe. Fluids were clarified by centrifugation at 14,000 g for 15 min at 4° C. The protein concentration was determined with the Bio-Rad Protein assay (Richmond, Calif.) with bovine serum albumin as a quantitative standard.

Determination of Elastase Activity in Wound Fluid

Elastase activity was determined by methods described previously. One hundred microgram amounts of protein were incubated in 1.0 ml of Hepes-NaOH buffer 100 mmole/L, pH 7.5, NaCl 500 mmole/L, 10% DMSO, containing 0 to 5 mg of cotton-bound fiber inhibitor. The heterogeneous reaction was incubated at room temperature while shaking vigorously. The inhibitor-protein mixture was then filtered through a 0.22 micron filter into a cuvette. The reaction substrate was added to each of the filtered samples to a final concentration of 100 $\mu$mole/L. Substrate hydrolysis was assessed by measuring $A_{410}$ at 5 min, 15 min, and 60 min after substrate addition. Purified neutrophil elastase was used to generate a standard curve.

Elastase Inhibition Kinetics

Reaction progress curves for inhibition of human neutrophil elastase (HLE) in the presence of fiber-inhibitor samples were generated. The weights of the cotton-bound inhibitor samples employed in the inhibition study were in the low milligram range (0.5 to 3.0 mg). Cotton samples formulated for the HLE inhibition effect a 0.01–0.7 $\mu$M inhibitor concentration. HLE concentrations in the reaction mixture were 0.5 and 0.2 units/mL, respectively. A dose response relation of enzyme inhibition was demonstrated in the reaction progress curve both for HLE.

The dose response of inhibition for HLE was apparent from the linear relation of a plot of reciprocal initial velocities ($1/v_o$) versus weight of fiber-inhibitor. It was likewise apparent that the dose response of inhibition for HLE using freely dissolved inhibitor is within a similar concentration range to that expected for release of inhibitor from the fiber into solution. Thus, the initial velocities ($v_o$) for the weighed fiber-inhibitor samples were within a comparable range to those observed for freely dissolved inhibitor concentrations assayed separately.

Biphasic reaction progress curves were observed for HLE by the free peptide chloromethyl ketone (CMK) and with peptide bound to fiber. This is also indicative of a slow-binding inhibitor. The reaction progress curves for slow-binding inhibitors may be described by the expression of equation 1.

$$P = v_s t + (v_o - v_s)[1 - \exp(-k_{obs} t)]/k_{obs} + d \quad (1)$$

Values for $k_{obs}$ were derived from this equation by applying it to the reaction progress curves of HLE. The $k_{obs}$ values for the pre-incubation experiments of fiber bound and freely dissolved inhibitor with enzyme were generated. The $k_{obs}$ for fiber-bound inhibition (table 1) of HLE demonstrate the same range and rate decrease as freely dissolved inhibitor.

Measurement of Enzyme Inhibition and Wound Fluid Activities

Inhibitory activities were measured by comparing $I_{50}$ values for the inhibitor bound and freely dissolved CMK inhibitor from each of the reaction progress curves. $I_{50}$ reflects the inhibitor concentration or fiber-inhibitor weight in suspension at 50% inhibition using the control inhibitor-free reaction as a benchmark of 100% activity. $I_{50}$ values were assigned for the inhibition of HLE based on a plot of initial rate versus freely dissolved inhibitor and fiber-inhibitor concentration. For HLE the plot of initial rate versus free inhibitor concentration reveals an $I_{50}$ of approximately 11 nM freely dissolved inhibitor and 0.6 mg of fiber-inhibitor as compared with 100 nM of released inhibitor (based on a semi-quantitative RPHPLC determination) by 0.6 mg of fiber-inhibitor.

Assessment of the fiber-inhibitor on elastase activity in wound fluid was performed by measuring substrate hydrolysis at fixed time points following incubation of fiber-inhibitor with HLE-containing wound fluid. A dose response of inhibition was evident when fiber-inhibitor samples ranging from 1 mg to 5 mg were incubated in the presence of wound fluid. Elastase activity levels decreased from enzyme activity in the absence of inhibitor (40–60 mU) to 5 mg of fiber inhibitor (0 to 10 mU). This decrease in elastase activity with increasing fiber weight demonstrates the inhibitory activity of the serine protease inhibitor as it is released into wound fluid.

Assessment of Elastase Sequences as Sequestrants

Chromatography was performed to measure the affinity of the cotton cellulose-bound recognition sequences for elastase, and the ability of the cotton fiber conjugates to sequester the elastase from an aqueous environment. Since the synthesis was performed on mercerized cotton, mercerized cotton was compared with unmercerized cotton as a chromatographic stationary phase for elastase elution. Less elastase was retained (4%) in the untreated mercerized cotton column compared to untreated unmercerized (12%). This might be expected since the crystallinity of the cotton fiber undergoes a change upon mercerization. Table 2 outlines the comparative levels of elastase retained, expressed as percent of retained elastase on the cotton columns. The comparative levels of elastase retained on the columns under physiological saline conditions suggests the ability to sequester elastase from wound fluid. Two series of elastase retention measurements were made based on the first injection of elastase to the freshly prepared column and subsequent percent elastase retained. The percent of retained elastase following the first injection was higher for all samples when compared with the repetitive injections. Conjugate I gave the highest retention of elastase. Fifty eight percent of elastase was retained on conjugate I as compared with the CMC control of thirty percent. Conjugate I is a COOH-terminal methyl ester of Val-Pro-Val attached to carboxymethylated cellulose at the amino-terminal valine. This results in the COOH-terminus being more accessible for enzyme binding. The cotton cellulose conjugate Val-Pro-Val-Gly sequence attached through the COOH-terminal glycine to cotton cellulose retained less elastase (26%) from the first injection. The percent elastase retained with repetitive injections followed a similar trend to the first-injected samples among the analogs tested. Conjugate I demonstrated the highest retention of elastase (37%).

Sequestration and Inhibition of Elastase Activity by Finished Cotton Gauze

The effect of a variety of cotton gauze finishes was tested to assess extraction of elastase from solution. Carboxymethylated, sulfonylated, phosphorylated, and oxidized cotton gauze were assayed as 50 and 75 milligram samples of type IV cotton gauze (used typically in patients with chronic wounds). Treated and untreated gauze samples were submerged in 1 milliliter of buffer containing 0.1 units/mL of human neutrophil elastase. The samples were allowed to incubate for one hour at room temperature, and the gauze samples were removed and placed in a press to drain unbound buffer and enzyme. The unbound buffer and enzyme fractions were combined and assayed for elastase activity as described above, the results of which showed that elastase activity was inhibited as shown in table 3. Inhibition of activity is evident from the decrease in protease activity observed with the increasing gauze concentrations in wound fluid.

TABLE 1

Kobs for fiber-bound inhibitors against human leukocyte elastase.

| Fiber mass (milligrams) | $K_{obs}$ (min$^{-1}$) |
|---|---|
| 0.5 | 0.0042 |
| 1.0 | 0.0046 |
| 2.0 | 0.042 |
| 3.0 | 0.638 |

TABLE 2

Elastase retention on peptido-cellulose columns.

| Cotton | Description of Cotton Conjugates | % Retained ± SD |
|---|---|---|
| I | Carboxymethylated Cellulose-Val-Pro-Val-OMe | 37 ± 0.71 |
| II | Val-Pro-Val-Gly-Cellulose | 26 ± 0.71 |
| III | Carboxymethylated Cellulose Cotton | 32 ± 2.12 |
| IV | Unmercerized Cotton Twill | 12 ± 1.63 |
| V | Cellulase-Treated Cotton | 15 ± 0.35 |
| VI | Val-Pro-Pro-Gly-Cotton (Cellulase-Treated | 12 ± 2.47 |
| VII | Mercerized Cotton Twill | 4 ± 1.41 |

Elastase was injected on to the cotton conjugate columns as described. Percent elastase retained represents the average of triplicate injections on the same columns.

Reaction rates ($v_o$) and protein analysis from gauze-soaked wound fluid. Comparison is between untreated (UT) gauze and dialdehyde cotton gauze (DAG) the preparation of which is shown in Example 5.

TABLE 3

| Gauze Per Vol. Fluid Mg gauze/ $\mu$L W Fluid* | UT Gauze Specific Adsorpt. ($\mu$g protein/ mg gauze) ± S.D.** | UT Gauze $V_0$ e-03 (s$^{-1}$) ± S.D.+ | DAG Specific Adsorpt. ($\mu$g protein/ mg gauze ± S.D.** | DAG $V_0$ e-03 (s$^{-1}$) ± S.D.+ |
|---|---|---|---|---|
| 2.5 | 8.74 ± 0.06 | 2.81 ± 0.068 | 7.42 ± 1.2 | 2.46 ± 0.038 |
| 7.5 | 1.10 ± 0.62 | 1.18 ± 0.047 | 3.49 ± 0.28 | 0.65 ± 0.028 |
| 10.8 | 1.69 ± 0.69 | 0.62 ± 0.129 | 2.82 ± 0.44 | 0.23 ± 0.14 |
| 14.2 | 1.60 ± 0.33 | 0.22 ± 0.057 | 2.69 ± 0.39 | 0.08 ± 0.03 |
| 17.5 | 1.40 ± 0.24 | 1.09 ± 0.137 | 1.83 ± 0.29 | NA*** |

*Mg gauze/$\mu$L wound fluid (w.f.) was calculated by dividing the gauze mass by the volume of the wound fluid (w.f.) used in the experiment. For example (75 mg gauze/3 mL diluted w.f.) × (1 mL diluted w.f./10 $\mu$L (0.01 mL) w.f.) = 2.5 mg gauze/$\mu$L w.f. The elastase activity (0.25–0.27 units) of the wound fluid used in these experiments was the same as shown in FIG. 5B.
**Specific adsorption of protein on gauze ($\mu$g protein/mg gauze) was determined by dividing the residual protein mass by the initial gauze mass. Redidual protein mass remaining on the gauze after exposure to wound fluid was calculated by subtracting the protein mass remaining in solution from the initial protein mass of the solution diluted 1:100: (wound fluid-:buffer: v:v). [Protein]$_{1:100\ solution}$ $\mu$g/mL × 3 mL = Initial protein mass; [Protein]$_{after\ exposure}$ $\mu$g/mL × (3.0 mL × 0.9) = Protein in solution after incubation; Initial protein mass − protein mass after incubation = Gauze-bound protein (residual protein).
***NA (No measurable rate or elastase activity).
+Reaction rates are reported as initial velocities ($v_o$) which were taken from the slope of the linear least-squares fit of absorbance-time data of the reaction progress profiles as described in the Materials and Methods section under Enzyme Assays. Data are mean ± SD of triplicate determinations. All are significant when compared within the five groups of protein and reaction rate data such that p < 0.05 and were determined by one-way ANOVA and analysis of variance.

We claim:
1. A wound dressing of the formula:

$$X—A \qquad (I)$$

wherein:
X is selected from:
films of a semipermeable or semi-occlusive nature;
hydrocolloids;
hydrogels;
foams;
impregnates;
polysacharide-containing matrices capable of ionically or covalently bonding active agents thereto, or having active agent compositioned with or upon; and
A is selected from the group consisting of:
pentafluorethylketone,
dihydroxylketone,
levulinate,
2,3 dialdehyde anhydroglucose,
glucose-6-citrate, and
2,3-dialdo-glucose-6-citrate.

2. The wound dressing of claim 1, wherein A is 2,3 dialdehyde anhydroglucose.

3. The wound dressing of claim 1, wherein A is glucose-6-citrate.

4. The wound dressing of claim 1, wherein A is 2,3 dialdehydo-glucose-6-citrate.

5. The wound dressing of claim 1, wherein A is pentafluoroethylketone.

6. The wound dressing of claim 1, wherein A is dihydroxylketone.

* * * * *